United States Patent [19]

Wright et al.

[11] Patent Number: 4,926,969

[45] Date of Patent: May 22, 1990

[54] SENSORY-DRIVEN CONTROLLER

[75] Inventors: Geoffrey D. Wright; Edmund Pirali, both of Baltimore, Md.

[73] Assignee: NeuroSonics, Inc., Baltimore, Md.

[21] Appl. No.: 272,949

[22] Filed: Nov. 18, 1988

[51] Int. Cl.$^5$ .............................................. A61B 5/04
[52] U.S. Cl. ..................................... 128/731; 128/745
[58] Field of Search ............................... 128/731–733, 128/745, 905

[56] References Cited

U.S. PATENT DOCUMENTS

| | | |
|---|---|---|
| 3,087,487 | 4/1963 | Clynes . |
| 3,893,450 | 7/1975 | Ertl ..................... 128/731 |
| 3,911,316 | 10/1975 | Feick et al. . |
| 4,109,145 | 8/1978 | Graf . |
| 4,140,997 | 2/1979 | Brady . |
| 4,149,716 | 4/1979 | Scudder . |
| 4,158,196 | 6/1979 | Crawford, Jr. . |
| 4,188,956 | 2/1980 | John ..................... 128/731 |
| 4,275,744 | 6/1981 | Thornton et al. .............. 128/731 |
| 4,293,855 | 10/1981 | Perkins . |
| 4,408,192 | 10/1983 | Ward et al. . |
| 4,533,346 | 8/1985 | Cosgrove, Jr. et al. . |
| 4,545,388 | 10/1985 | John ..................... 128/731 |
| 4,558,315 | 12/1985 | Weiss et al. . |
| 4,562,432 | 12/1985 | Sremac . |
| 4,565,999 | 1/1986 | King et al. . |
| 4,603,703 | 8/1986 | McGill et al. .............. 128/731 |
| 4,605,927 | 8/1986 | Katz et al. . |
| 4,632,126 | 12/1986 | Aguilar . |
| 4,642,610 | 2/1987 | Smith, III . |
| 4,648,052 | 3/1987 | Friedman et al. . |
| 4,682,159 | 7/1987 | Davison . |
| 4,697,598 | 10/1987 | Bernard et al. . |
| 4,705,049 | 11/1987 | John . |
| 4,739,772 | 4/1988 | Hokanson et al. .............. 128/731 |
| 4,746,913 | 5/1988 | Volta . |

OTHER PUBLICATIONS

MacLaurin, William, "Talk Via Brain Waves," *Science News Letter*, Oct. 31, 1964.
"Mind Power: Alpha," *Radio-Electronics*, Jul. 1976.
"Mind Power: Alpha, Part IV," *Radio-Electronics*, Oct. 1976.
Sobell, Nina and Trivich, Michael, "Brainwave Drawing Game," IEEE, 1981.
Zweig, Connie, "Mind Reading (Almost)," *Omni*, Feb., 1985.
Dymek et al., "A Goggle System Using Electrically Activated Crystal Shutters", Conf. Proc. of the 7th NE Bioeng. Conf., 11-1979, pp. 45–48.

*Primary Examiner*—Angela D. Sykes
*Attorney, Agent, or Firm*—Bacon & Thomas

[57] ABSTRACT

A non-motive system for enabling a person to carry out a function includes circuitry designed to detect evoked-response potentials as a result of stimuli presented to the person. Each element of the stimulus corresponds to an external factor or function, so that the person attending to a particular element may communicate his desire that the external factor or function corresponding to that element be carried out merely through the detection of his brain wave response to the stimulus. The brain wave response is detected by electrodes, conditioned, and correlated with a precalibrated set of response template signals to derive the element attended by the subject, and thereby cause the indicated factor or function to be carried out.

16 Claims, 3 Drawing Sheets

SENSORY-DRIVEN CONTROLLER

BACKGROUND OF THE INVENTION

1. Field of the Invention

This invention relates generally to brain-wave analysis and brain-based control, and, more specifically, to systems designed to perform various functions based upon evoked-response potentials.

2. Description of the Related Art

The present invention is designed to allow a subject to perform various controls and functions through the detection and analysis of electroencephalogram (EEG) response to stimuli. Prior art systems that attempt to enable a subject to carry out functions through non-motive means have been employed with a limited amount of success. Among those related to the operation of the present invention, the most successful have been eye-tracking systems that utilize laser beams to determine eye position of a person, to thereby enable the person to control various systems based upon the position of his eyes. Such systems, however, suffer from inaccuracies based primarily upon involuntary muscle activity, of which, for example, disabled persons are often afflicted. The basic theory and technology behind evoked-response potentials (ERPs), including their creation and detection, are well-established and widely discussed in the literature. ERPs are electrical potentials that occur in the human brain in response to an external physical event. By analyzing the ERP, or any or all of its components, data can be derived for analysis. Control techniques employing ERP technology are theoretically more accurate and predictable than the above-mentioned eye-tracking systems, and therefore promise more precise applications since the data is obtained directly from brain functions and mental processes rather than from gross muscular movements.

One system directed towards function control based upon EEG responses to stimuli is disclosed in U.S. Pat. No. 4,651,145 to Sutter, and in various publications by the same inventor but utilizes different algorithms for data presentation and analysis than does the present invention.

SUMMARY OF THE INVENTION

The present invention overcomes the problems of the prior art by providing a new system for detecting the point of attention of a person responding to a stimulus. The stimulus may be any sensory stimulus capable of producing a detectible EEG response, including visual or auditory. A sensory stimulus corresponding to a particular factor or function is provided to the subject to evoke an EEG response in the subject's brain. The EEG response is transmitted via electrodes or other known EEG-detecting devices to a system that amplifies and filters the EEG signal, and then converts it to digitized form for presentation to signal processing circuitry.

Preferably, a plurality of stimuli are provided simultaneously, each stimulus corresponding to an external factor or function. While the subject attends to a particular stimulus in order to thereby communicate a command to the signal processing circuitry and subsequent control system, the signal processor determines from the EEG responses which stimulus the subject is attending. The received EEG signals are conditioned to reduce noise and to suppress artifacts, and the subsequent signals are correlated with a precalibrated set of response template signals to determine the correlation between the EEG response and the template signals. This signal analysis algorithm enables the signal processor to determine which stimulus the subject attends, and thereby cause a control system to carry out a function corresponding to the attended stimulus.

DETAILED DESCRIPTION OF THE PREFERRED EMBODIMENTS

An illustrative application for the invention described herein is its use in the fields of aids for the disabled. As such, the invention should not be construed as being limited to the field of aids for the disabled, but instead, should be understood as having broader applications to non-motive control, and more particularly, to EEG-based control based upon evoked-response potentials.

Figure 1:
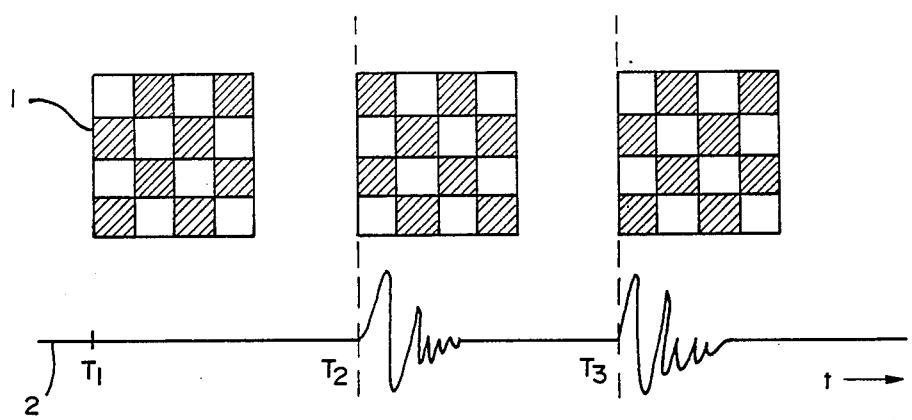
FIG. 1 shows one example of a visual stimulus that may be used to evoke an EEG response according to the teachings of the present invention.

FIG. 1 shows a simple example of a known way to produce an electroencephalogram (EEG) response from a subject. A stimulus is represented by a square checkerboard pattern 1, which is adapted to alternate its color between, e.g., white-black-white and black-white-black, i.e., to "invert" its color pattern according to a predetermined scheme. Responsive to each change in state, a subject viewing the pattern emits an EEG response that may be detected using known methods. A time line 2 shown beneath these squares illustrates how a transcribed EEG might be shown for a person viewing the alternation of state. At time $T_1$, the stimulus is in its first state (e.g., white-black-white, etc., from left to right in the upper row). At time $T_2$, the state has changed (to black-white-black, etc.), and an EEG response is evoked in the viewer. At time $T_3$, the stimulus state has reverted back to its first state, and another EEG response has been evoked. Additional examples of visual stimuli that may be used include stimuli whose elements are altered by changing their sizes or their pattern. Other visual stimuli that evoke detectible EEG responses will be apparent to one of ordinary skill in the art.

The EEG response shown is merely illustrative, and is therefore significant only in its relationship to the change of state of the stimulus. In actuality, the transcribed EEG response will appear differently for different persons, as well as for different stimuli. Furthermore, on a true time line, the EEG response will appear delayed from the actual change of state by an amount equivalent to the delay required for the viewer to sense the change of state and to respond, which also varies from subject to subject. The color-changing square is also merely used as a representative stimulus; as discussed in greater detail below, other stimuli may be used to evoke an EEG response in a subject, and such stimuli are not limited to color-changing, inverting, or flashing squares, nor are they limited to state-changing squares or even to visual stimuli.

Another means for evoking EEG response is the successive presentation of elements. For example, element no. 1 (e.g., a flash of light) may be presented, followed by the presentation of element no. 2 (e.g., a second flash of light spatially separated from the first), such that a response is evoked, although no alteration of state has occurred.

Additionally, the combination of stimuli may be utilized to an almost limitless extreme to heavily encode the presented targets with information. The various frequencies of stimuli presented may be designed to interrelate (e.g. one target inverts only when a specified two other targets simultaneously invert), thereby providing both a high rate of information transfer and a very high signal-to-noise ratio, which allows fast, real-time analysis by pattern matching. The concept and analysis are reminiscent of beat analysis and interference pattern analysis, which may themselves also represent bases for analysis.

A preferred embodiment of the invention, however, is illustrated as utilizing a visually evoked response, using a plurality of inverting squares. An inversion, thus, is defined as being any time the color of a square changes from white to black or vice versa, or, in a much broader sense, as any time the state of the stimulus is changed so as to evoke an EEG response in a subject.

The above-described EEG response of a subject viewing an inverting square is best elicited and most easily detected if the subject focuses on the stimulus, or target. Electrodes attached to the surface of a subject's scalp at specific sites (for example, for visual stimuli, the $O_z$ and $F_z$ sites for one-electrode placement, or the $O_1$, $O_2$, and $F_z$ sites for two-electrode placement), as is known in the prior art, provide the means for detecting an EEG response to a visual stimulus.

Figure 2:
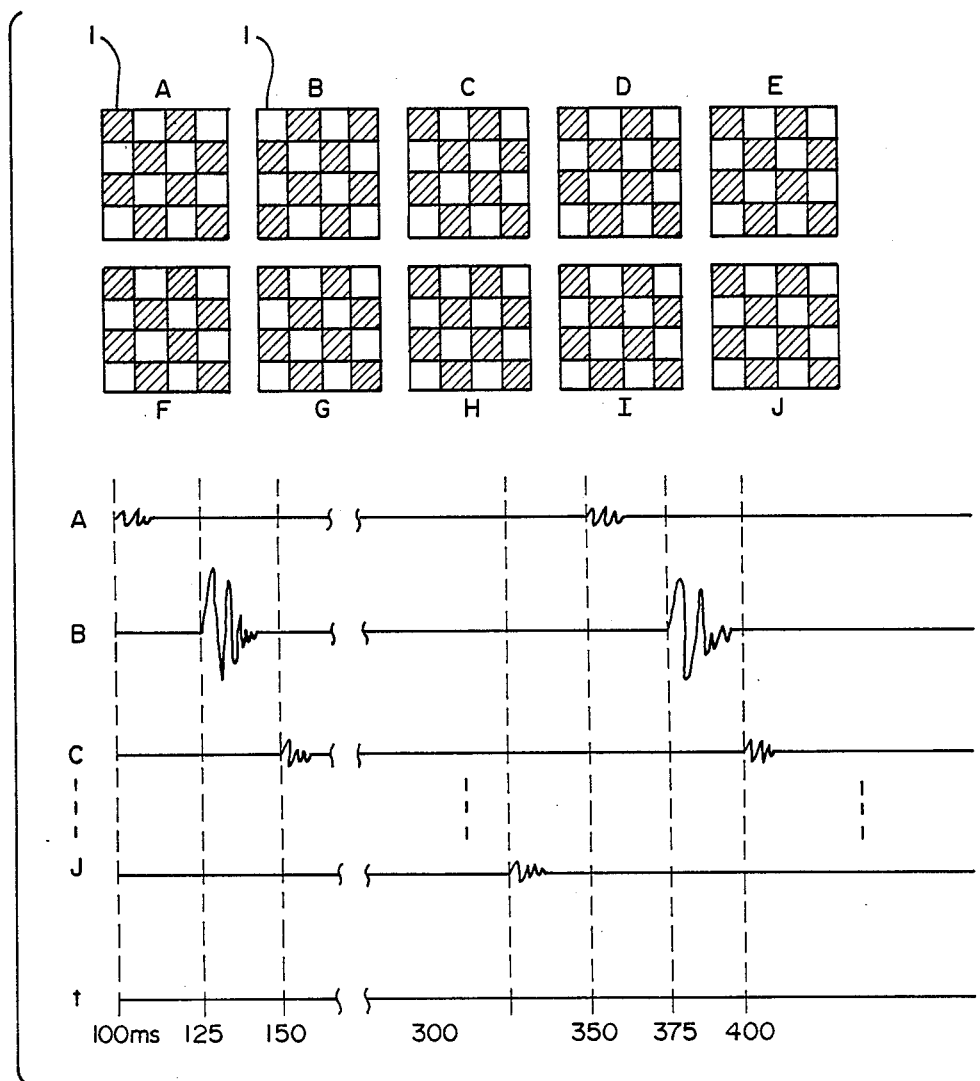
FIG. 2 illustrates the phase relationships among a plurality of stimuli as taught by the present invention.

This known principle can be expanded to a system that detects which one of a plurality of targets a viewer is viewing. The sample shown in FIG. 2 is one display of multiple targets of which a particular one being viewed by a subject may be determined by the system constructed and operated according to the teachings of the invention. One method for determining which target is being viewed is to invert each target separately and test the EEG response, and then to move on to the next target. This approach, however, is too slow for practical use. By staggering the repeated inversions of targets in time, sequential inversion may still be utilized at a higher rate of speed, but without requiring a response test after each inversion.

Using the example shown in FIG. 2, if each of the 10 targets 1 is inverted 4 times per second (4 Hz), a period of 250 ms passes between successive inversions of a given target. For 10 targets, therefore, the first target is inverted at time 0 ms, the second at time 25 ms, the third at time 50 ms, and so on for all targets. When the tenth target is inverted at time 225 ms, the sequence is complete, so that the first target is again inverted at time 250 ms. A sequence may be repeated over and over, so that a plurality of periodic EEG responses for each target is sensed by the electrodes and delivered to signal processing circuitry, where each target's response has the same frequency (4 Hz) as each other target, but is out of phase by 25 ms with its preceding and succeeding target's response.

By taking into account the inherent latency of the subject's brain response to the stimulus, the specific target viewed by the subject may be determined. For example, if a given subject's characteristic evoked response potential (ERP), or EEG response to a stimulus, has a latency of 100 ms (determined during a calibration procedure to be described more fully below), his ERP would occur at a time 100 ms after the actual stimulus time (e.g. at time 100 ms if attending target A, 125 ms for target B, etc.). This method of temporally staggering the targets is somewhat limited by the slight irregularity of latency in each subject's ERP response.

As presently understood, successive inversions preferably occur no more frequently than approximately 20-25 ms on average for accurate resolution by the processing system. The frequency may be increased under certain circumstances, depending upon the subject and the stimulus used. Using 25 ms as the interval, if a group of targets is to be inverted at 4 Hz, therefore, no more than 10 targets are distinguishable because no more than 10 targets may invert at 25 ms intervals within a time period of 250 ms. Slower frequencies may be used in order to include more targets, but higher frequencies and fewer targets enable cleaner and faster responses and more accurate processing determinations.

The EEG time lines shown in FIG. 2 illustrate the evoked-response nature of the inversion-response design. Each time line represent the EEG response due to inversion of the individual targets. Taking target B as the viewed target, its time line shows the highest amplitude response.

Because the human brain constantly produces EEG activity, any system designed to elicit specific information related to ERP events must be designed to factor out EEG activity unrelated to the ERP event. Among those EEG signals that invade the ERP response are those EEG signals related to muscle movements, unrelated brain wave activity, and evoked responses from stimuli other than the stimulus to which the subject is currently attending. Some of these sources produce EEG patterns that are easily distinguishable from the ERP, but others produce patterns that are so similar or invasive to the ERP that the ERP may not be easily divined.

In order to prevent false positive responses, the invention includes a method of averaging multiple inversions of the target. In other words, rather than attempting to determine the viewed target based upon a single inversion of each target and the subsequent response, the sequence of inversions may be repeated, and the results averaged. As for most repeatable measurements subject to statistical averaging, the greater the number of trials, the more accurate the results. According to the teachings of the present invention, three trials represents the preferred minimum number of trials for adequately rejecting false positive responses, so that a determination of viewed target may be made with sufficient accuracy. Put differently, three trials offer an acceptable increase in the signal-to-noise ratio for a preferred form of the invention.

Using a 4 Hz rate, the system needs less than one second to acquire enough data for accurate analysis. Adding targets while simultaneously, and necessarily, slowing the frequency to, for example, 2 Hz, requires more than one second to complete three trials and to therefore acquire enough data for accurate analysis. This tradeoff (speed of analysis v. number of targets) places limits on a system utilizing only phase relationships for analysis.

A solution to the tradeoff is to add target regions having different frequencies. Each such frequency group contains a plurality of targets inverting at a common frequency, but with different respective phases, as described above with respect to FIG. 2, with all targets within each frequency group being distinguishable by the above-mentioned averaging method. By providing each frequency group with a different frequency, the system can differentiate between frequency groups and, within each frequency group, among targets to derive a single viewed target from a plurality of targets from a plurality of frequency groups.

Figure 3:
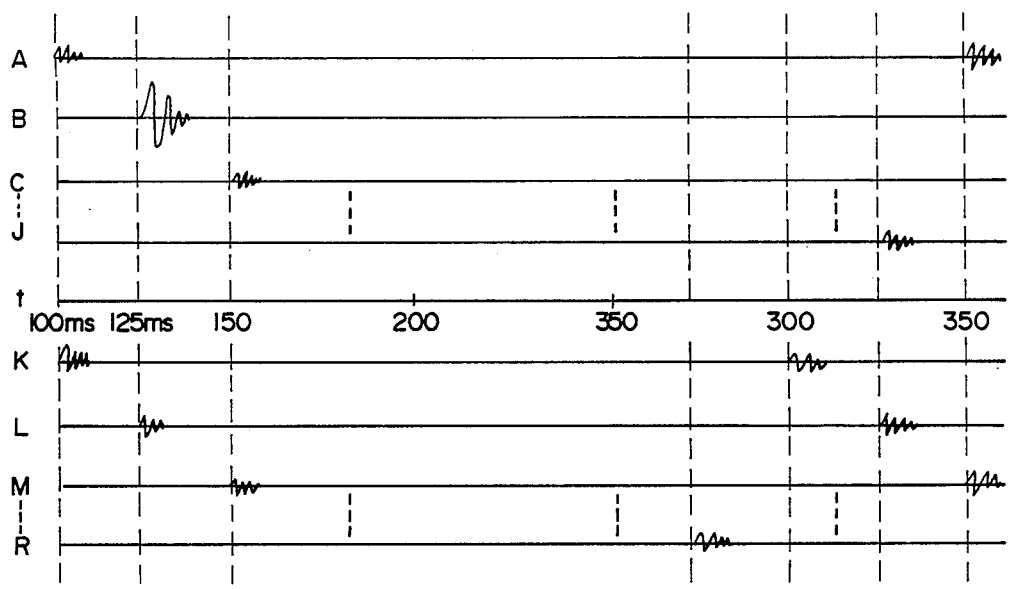
FIG. 3 shows the phase and frequency relationships among a plurality of EEG responses evoked by a plurality of stimuli whose characteristics are altered at various relative phases and frequencies.

Referring to FIG. 3, an example of the analysis method is illustrated. FIG. 3 shows an EEG response for 10 targets inverting at 4 Hz each, above the time line t. Below the time line t is shown a similar EEG response for a frequency group inverting at 5 Hz, with 8 targets instead of 10. Target A (4 Hz group) inverts at times 100 ms, 350 ms and 600 ms (including a 100 ms latency period) to complete the three trials desired for accurate analysis. Simultaneously, target K (5 Hz group) inverts at times 100 ms, 300 ms and 500 ms. EEG data collected from time 0 through time 850 ms are analyzed to determine which target the subject is attending.

Using the above averaging techniques, any ERP response generated from one frequency group will average out when averaged at a different frequency. That is, if the subject is looking at target K (5 Hz) with a subject ERP latency of 100 ms, the ERP response occurs at 100 ms, 300 ms, etc. When averaging the trials modulo 250 ms (4 Hz averaging), each ERP response from the 5 Hz group will be shifted earlier by 50 ms in each trial, and will therefore not combine with responses from other trials, so that when all data are divided by number of trials, the overall amplitude of the shifted responses will drop by a factor of three, and create a new mutated non-ERP shape. A threshold imposed by the system will not be met by such a small response, so that an ERP response in the 5 Hz group will have no effect in a determination in the 4 Hz group.

The same effect will occur whenever averaging is carried out across frequency groups, although analysis is slightly more complicated when ERP responses cross frequency groups that are multiples of one another. Of course, the 5 Hz frequency signals will occur in the same position within each trial when viewed modulo 200 ms, so that analysis within each frequency group is carried out exactly as described above with respect to FIG. 2.

By using these techniques of averaging, many different frequency groups, all slightly shifted in frequency, may be included within practical limits. One such practical limit is that targets within higher frequency groups will have a faster response and analysis time than those within slower groups. This limit, however, can be used to advantage in certain applications. For example, just as a conventional QWERTY typewriter keyboard is designed so that the most-used keys are easiest to access, the present invention may be designed so that the most-used functions are assigned to the fastest targets, and the least-used functions to the slowest targets. Furthermore, in order to overcome the problem of frequency groups that are at integral multiples of one another, such dependent groups may be combined to further define a target by divining the subject's state of attention with respect to that target with regard to its inversion at times at which two or more other targets are also inverting.

Figure 4:
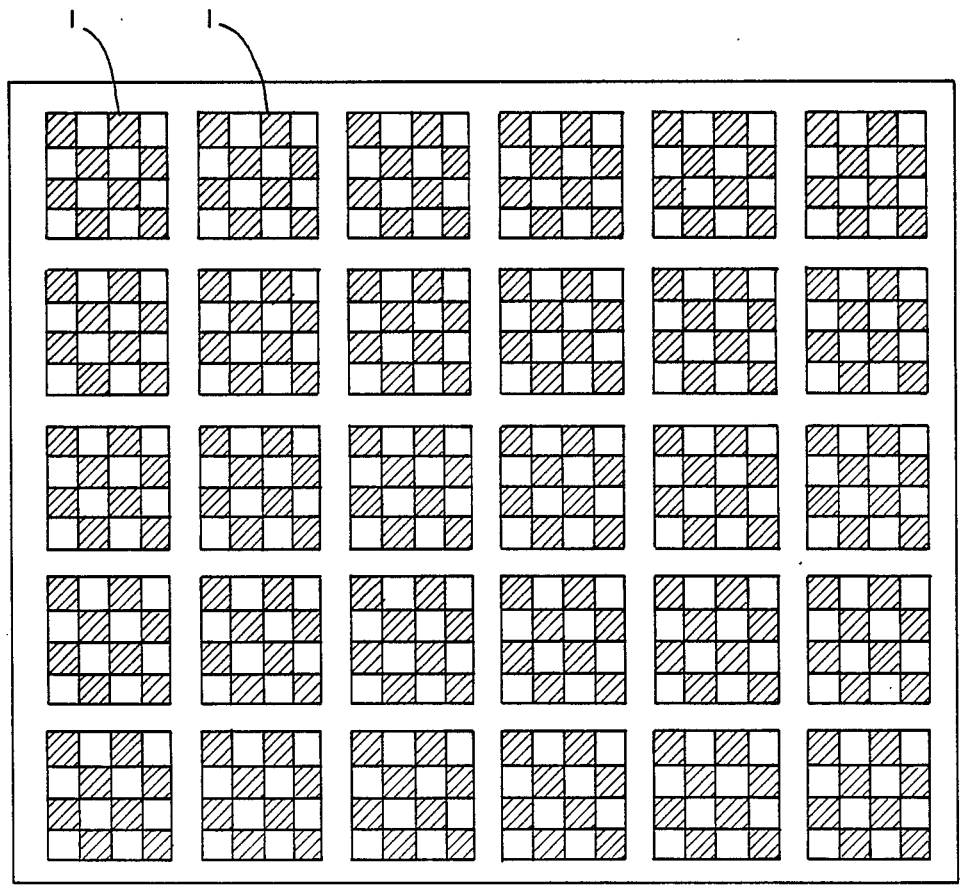
FIG. 4 shows an example of a display screen that may be used in accordance with the teachings of the present invention.

FIG. 4 shows an illustrative example of a display screen 3 used in conjunction with the first embodiment of the present invention. Thirty different targets 1 are shown, representing a plurality of frequency groups. For example, 12 targets may comprise a 3.3 Hz group, 10 targets a 4 Hz group and 8 targets a 5 Hz group. The specific number and frequency of each group, of course, is arbitrary; any number of frequency groups that may be practically shown on a single display screen or on multiple display screens is possible.

Because each subject's ERP response is different from that of other subjects, a template for each differing category of stimulus must be built using a calibration process as described below.

For this calibration process, only one target of a given stimulus category (for example, frequency group) is shown to the subject. Data for a number of trials, which, as for the actual sensory process described above, will be analyzed with increasing accuracy as the number of trials increases, are collected. The number of trials during calibration is usually larger than the number of trials used during the pattern-matching run in order to obtain the most characteristic ERP response for each category of stimulus. Preferably, at least 20 trials are run for the calibration procedure, although fewer trials may achieve more accurate results for certain individuals who prefer shorter calibration times due to fatigue or a short attention span. In such cases, a single run of fewer trials may be adequate to establish a response template, but if, for example a person having a short attention span cannot produce an adequate response template with fewer trials, a plurality of trial runs each having fewer than 20 trials may be carried out, with the results compiled as though all trials were carried in one continuous run.

When the data for all calibration trials are collected, the average for all trials is calculated to obtain a "primary template". The primary template is a characteristic ERP response for the subject, but does not account for the subtle time variations that occur from one trial to the next. Each individual calibration trial is therefore cross-correlated to this primary template, with predetermined time shift restrictions, to obtain the best correlation. A second average is then calculated from these cross-correlated trials that is usually considerably more defined, and has accounted for the slight human response time variations. This "secondary template" is used as the template for that stimulus category.

Figure 5:
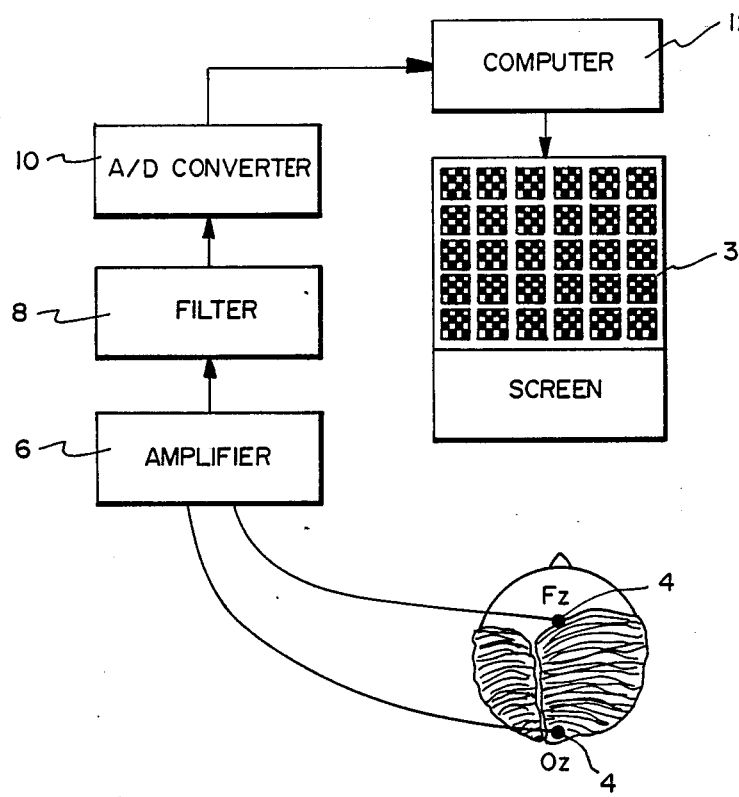
FIG. 5 shows a schematic of the present invention from electrodes attached to a subject to a computer and display screen.

The signal processing circuitry for receiving signals from a subject's electrodes and from the display is preferably digitally-based, and is shown in block diagram form in FIG. 5. EEG signals taken from the subject at the electrodes 4 are amplified and filtered by amplifier stage 6 and a filter stage 8 to enhance the averaging and correlation procedures that are incorporated later during processing.

After filtering, the signals are digitized in an analog-to-digital converter 10 and level shifted before being delivered to data averaging circuitry within computer 12 in order to remove any DC bias. While partially described above, the particular data averaging utilized by the invention may be more fully described as a process of adding corresponding points from repeated trials and dividing by number of trials, to obtain an average, or mean, of the overall signal. The primary use of averaging is to improve the signal-to-noise ratio, noise being defined as any signal that is not useful in correlating an EEG response with a stimulus to which a subject is attending. The most common noise sources, as alluded to above, are background spontaneous EEG activity and muscle movement artifacts. Assuming that all non-ERP related signals are white noise or pink noise (valid for this system), the average of all non-related signals approaches zero as the limit of the number of trials approaches infinity. EEG signals that are related to the stimulus-response, of course, reinforce each other.

Additional signal processing methods are used for purposes of noise reduction and artifact suppression. Any of these additional signal processing methods may be used instead of the averaging method outlined above, or in addition to the averaging method. A second method is to reject the data of entire trials based upon certain criteria. For example, if the mean value of a trial is displaced too far from a base line (based upon a predetermined limit), then that trial has a large DC offset. If this offset is too large, either in a negative or positive direction, it signifies an overloaded amplifier or a muscle movement artifact. Those trials having such a large DC offset are rejected completely in order to entirely discard movement artifacts.

Another technique is to compare the responses to the target stimulus from each hemisphere of the brain. If the signal is a valid ERP response (i.e. responsive to the stimulus alone), then the signals from both hemispheres will be very similar. If, however, the signal is an artifact, then the correlation of the two signals will be very low, as the reflection of a muscle movement artifact in signals from both hemispheres is extremely unlikely. Detecting EEG responses from each hemisphere of the brain adds the advantage that twice as much data may be retrieved per unit time, in comparison with detection from one site.

Figure 6:
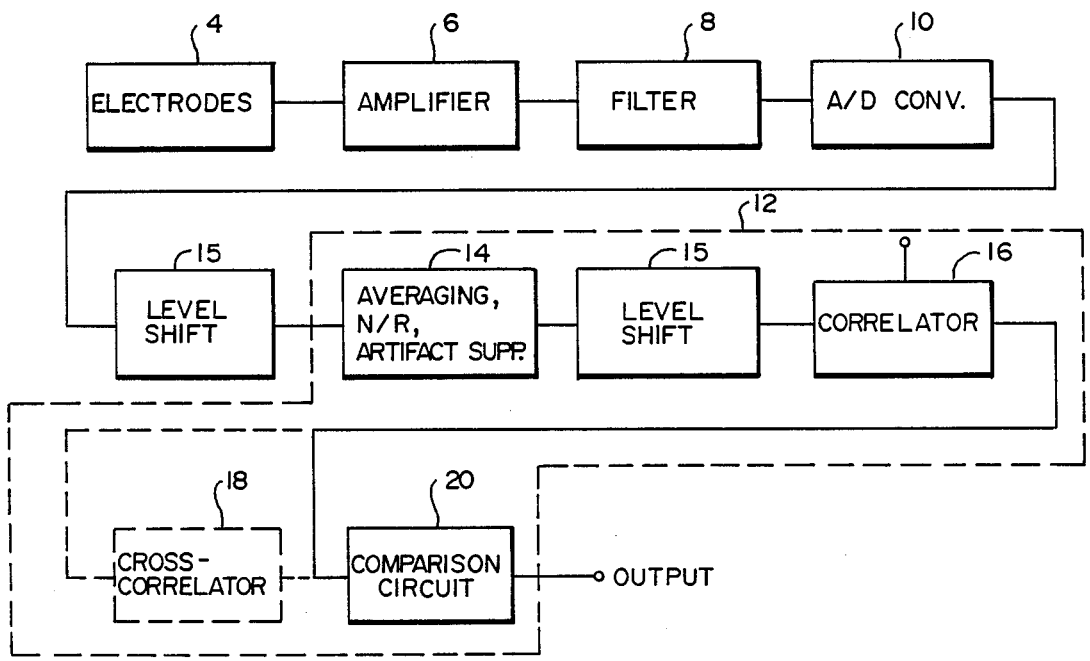
FIG. 6 illustrates a block diagram of the circuitry employed in carrying out the present invention.

The processing techniques just described are used for both the template-establishing procedure and for the actual operational run, which data are analyzed using circuitry schematically illustrated in FIG. 6. During the actual run, the signal that emerges from one or more of these noise reduction and artifact suppression stages generally indicated at 14 is correlated in correlator 16 with the calibrated response template signals to determine which template signal corresponds most closely with the measured ERP signal. Level shift stages 15 are optional, and may be employed at any of various stages in the circuit to remove any DC bias, including before and after processing stages. For each template signal, if the template signal and the ERP signal are not at all related, the correlation will be zero. If the two signals are identical in shape and have very close or identical phase, the correlation will be a large positive number dependent upon the average amplitude of each signal. If the signals are identical but are 180 degrees out of phase with each other, the correlation will be a large negative number dependent upon the average amplitude of each signal. In order to remove the effect of signal amplitude from the correlation value, the correlation value is normalized by dividing the correlation coefficient by a divisor to change its range from $-1$ to $+1$.

Optionally, the average signal may be cross-correlated at 18 with each individual trial to obtain the best correlation with the average, and to account for slight time variations in ERP response from trial to trial, and a new average calculated. This process enhances the ERP response and removes time variabilities inherent in human responses. This cross-correlation step improves response in some subjects, but not others. The output signal is then correlated with the template signals as above.

By comparing the correlation coefficient with the auto-correlation of the template at 20, the subject's point of attention may be determined. Where the comparison shows that the correlation coefficient exceeds a threshold percentage, set by the system operator or by an autocalibration routine, of the auto-correlation, the subject has been attending a target of the frequency corresponding to that template signal. From the value of the correlation coefficient, the exact phase of the target that evoked the response in the subject may be determined, thereby revealing the attended target.

Since the only difference in the characteristics of targets in a given frequency group is the phase, one template may be used for all targets of the same frequency group. If for some reason the subject has some difficulty with a given target, that target can be specifically used for the calibration procedure. The calibration data may be stored on a more permanent medium (such as magnetic discs) than the pattern-matching run data (which are preferably stored in RAM), as the calibration data generally may be used over time, and even with slightly changing electrode placements.

Although the invention has been described with respect to the specific embodiment utilizing visual stimuli, the same basic invention may be carried out using auditory stimuli, with relatively minor modifications to the system. For example, electrode placement must be changed to locations on the subject's body where aural-evoked responses are known to best be detected. The basic algorithms for detecting and analyzing auditory-evoked potentials (AEPs) are the same as those for detecting and analyzing ERPs, but, of course, size, shape, color, etc. are inappropriate characteristics for analysis of AEPs. Tone, timbre, volume, etc. are examples of useful characteristics that may be changed to evoke EEG responses. As for the visual ERPs, the AEPs are analyzed for phase and frequency differences to determine the particular audio target to which the subject is attending.

Additionally, AEPs and ERPs may be combined to further expand the range of stimuli and number of targets for use in a system designed according to the basic teachings of the present invention.

One application of the invention set forth above is to aid a disabled person in performing various functions that normally require human motor capability. For example, a conventional wheelchair may be outfitted with an essentially portable display screen, including circuitry and/or software to carry out the above-described detection and analysis. Each target displayed on the screen may be programmed to represent a particular function, so that the subject enables a particular function to be carried out by gazing at the target corresponding to the function. For example, a single target may correspond to the opening of an elevator door, while a second target may correspond to closing the elevator door. The subject preferably is situated in front of the elevator door, and gazes upon the target corresponding to opening of the door. The system described above communicates the function indicated by the subject's point of attention, and commands a transmitter located at the wheelchair to transmit a signal to a receiver located at the appropriately outfitted elevator.

The elevator door then opens, allowing the subject to move into the elevator, at which point the subject gazes upon the target corresponding to a "close door" function, which is then carried out as the "open door" was carried out. The transmitter, receiver and associated circuitry necessary to carry out the particular function are all derived from known devices.

Various modifications of the invention discussed in the foregoing disclosure will become obvious to one of ordinary skill in the art. Those modifications that basically rely on the teachings through which the invention has advanced the state of the art are properly considered within the spirit and scope of the invention.

We claim:

1. A method for detecting the point of attention of a subject who is attending to a stimulus, comprising the steps of:
    establishing a calibrated response template unique to the subject representing the correspondence between a stimulus and an evoked response;
    providing a stimulus for evoking an EEG response in a subject;
    detecting the EEG response evoked from the subject by the stimulus;
    mathematically corelating the EEG response with the template to derive the template response that corresponds to the EEG response; and
    determining the point of attention of said subject from said mathematical correlation.

2. A method for detecting the point of attention of a subject who is attending to a stimulus as claimed in claim 1, wherein said stimulus is encoded to represent an external factor.

3. A method for detecting the point of attention of a subject who is attending to a stimulus as claimed in claim 1, wherein said calibrated response template is substantially time-invariant.

4. A method for detecting the point of attention of a subject who is attending to a stimulus as claimed in claim 1, wherein said EEG response is detected simultaneously from both hemispheres of the brain.

5. A method for detecting the point of attention of a subject who is attending to a stimulus as claimed in claim 1, wherein the stimulus comprises a plurality of elements, and wherein the EEG response is a composite response comprising responses evoked individually from each element.

6. A method for detecting the point of attention of a subject who is attending to a stimulus as claimed in claim 5, wherein the EEG responses evoked from the stimulus elements have relative phase differences.

7. A method for detecting the point of attention of a subject who is attending to a stimulus as claimed in claim 5, wherein at least two individual responses from two elements have relative frequency differences.

8. A method for detecting the point of attention of a subject who is attending to a stimulus as claimed in claim 1, wherein the EEG response has a characteristic that varies depending upon the stimulus provided.

9. A method for detecting the point of attention of a subject who is attending to a stimulus as claimed in claim 1, wherein the stimulus comprises at least one element having a sensible characteristic, and wherein the stimulus evokes the EEG response by altering the sensible characteristic of the element.

10. A method for detecting the point of attention of a subject who is attending to a stimulus as claimed in claim 9, wherein the characteristic is a visual characteristic.

11. A method for detecting the point of attention of a subject who is attending to a stimulus as claimed in claim 10, wherein the characteristic is color.

12. A method for detecting the point of attention of a subject who is attending to a stimulus as claimed in claim 10, wherein the characteristic is the external shape of the element.

13. A method for detecting the point of attention of a subject who is attending to a stimulus as claimed in claim 1, wherein the stimulus comprises a plurality of elements each having a visible characteristic, said elements forming a visible pattern, and wherein the stimulus evokes the EEG response by altering the pattern.

14. A method for detecting the point of attention of a subject who is attending to a stimulus as claimed in claim 1, wherein the stimulus is a visual stimulus.

15. A method for detecting the point of attention of a subject responding to a stimulus, comprising the steps of:
    providing sensors for sensing the EEG response of a subject to a stimulus, said sensors providing a sensor response signal comprising at least two trial electrical signals representing said EEG response;
    conditioning the sensor response signal, including amplifying, filtering and digitizing to produce a conditioned output signal;
    processing the conditioned signal to reduce noise and suppress artifacts, thereby producing a processed evoked-response potential signal representing the EEG response;
    deriving a response template for comparison with the processed evoked-response potential;
    mathematically correlating the processed evoked-response potential signal with the response template to determine the similarity in at least one aspect between the processed evoked-response potential signal and the response template, and providing a correlated output signal representing the degree of similarity between the two signals; and
    deriving the point of attention indicated by the correlated output signal.

16. A system for determining the point of attention of a subject responding to a stimulus, comprising:
    sensor means for sensing an EEG response evoked by a stimulus and for producing an electrical signal unique to that stimulus;
    amplifier means for receiving and filtering the amplified sensor signals;
    filter means for receiving and filtering the amplified sensor signals;
    digitizing means for receiving and digitizing the filtered signal;
    means for reducing noise and suppressing artifacts in the digitized filtered signal and to output an evoked-response potential signal;
    template means for providing a response template for comparison with the evoked-response potential signal;
    correlator means for eliciting signal differences between the evoked-response potential signal and the response template and to output a correlator output signal; and
    means for deriving the point of attention indicated by the correlator output signal.

* * * * *